(12) United States Patent
Ferrari

(10) Patent No.: US 12,064,649 B2
(45) Date of Patent: Aug. 20, 2024

(54) ULTRASOUND PROBE FOR TREATING EXTERNAL BODY TISSUES

(71) Applicant: BIOTEC ITALIA S.R.L., Dueville (IT)

(72) Inventor: Fulvio Ferrari, Padua (IT)

(73) Assignee: BIOTEC ITALIA S.R.L., Dueville (IT)

(*) Notice: Subject to any disclaimer, the term of this patent is extended or adjusted under 35 U.S.C. 154(b) by 370 days.

(21) Appl. No.: 17/425,912

(22) PCT Filed: Jan. 28, 2019

(86) PCT No.: PCT/IT2019/000004
§ 371 (c)(1),
(2) Date: Jul. 26, 2021

(87) PCT Pub. No.: WO2020/157778
PCT Pub. Date: Aug. 6, 2020

(65) Prior Publication Data
US 2022/0193458 A1    Jun. 23, 2022

(51) Int. Cl.
*A61N 7/02*    (2006.01)
*A61N 7/00*    (2006.01)

(52) U.S. Cl.
CPC ........ *A61N 7/02* (2013.01); *A61N 2007/0034* (2013.01); *A61N 2007/0065* (2013.01); *A61N 2007/0091* (2013.01)

(58) Field of Classification Search
CPC .... A61N 2007/0034; A61N 2007/0065; A61N 2007/0091; A61N 7/02
See application file for complete search history.

(56) References Cited

U.S. PATENT DOCUMENTS

| 5,762,066 A | 6/1998 | Law et al. |
| 2004/0082859 A1* | 4/2004 | Schaer ............... A61B 18/1492 600/459 |
| 2012/0053468 A1 | 3/2012 | Griffin et al. |
| 2014/0058294 A1 | 2/2014 | Gross et al. |
| 2015/0217141 A1* | 8/2015 | Barthe .................... A61N 7/00 601/2 |
| 2019/0134430 A1 | 5/2019 | Jeong |

* cited by examiner

*Primary Examiner* — Amelie R Davis
(74) *Attorney, Agent, or Firm* — DUANE MORRIS LLP; Gregory M. Lefkowitz; Joaquin Hernandez

(57) ABSTRACT

An ultrasound probe for treating body tissues, which includes a focused ultrasound emitter arranged inside a main body provided with a porn that can be gripped, and a means for connection to a remote unit for the power supply and control of the probe. The particularity of the present invention resides in that it includes a means for adjusting the penetration depth of a beam of focused ultrasound, emitted by the emitter, in a tissue of a patient.

7 Claims, 4 Drawing Sheets

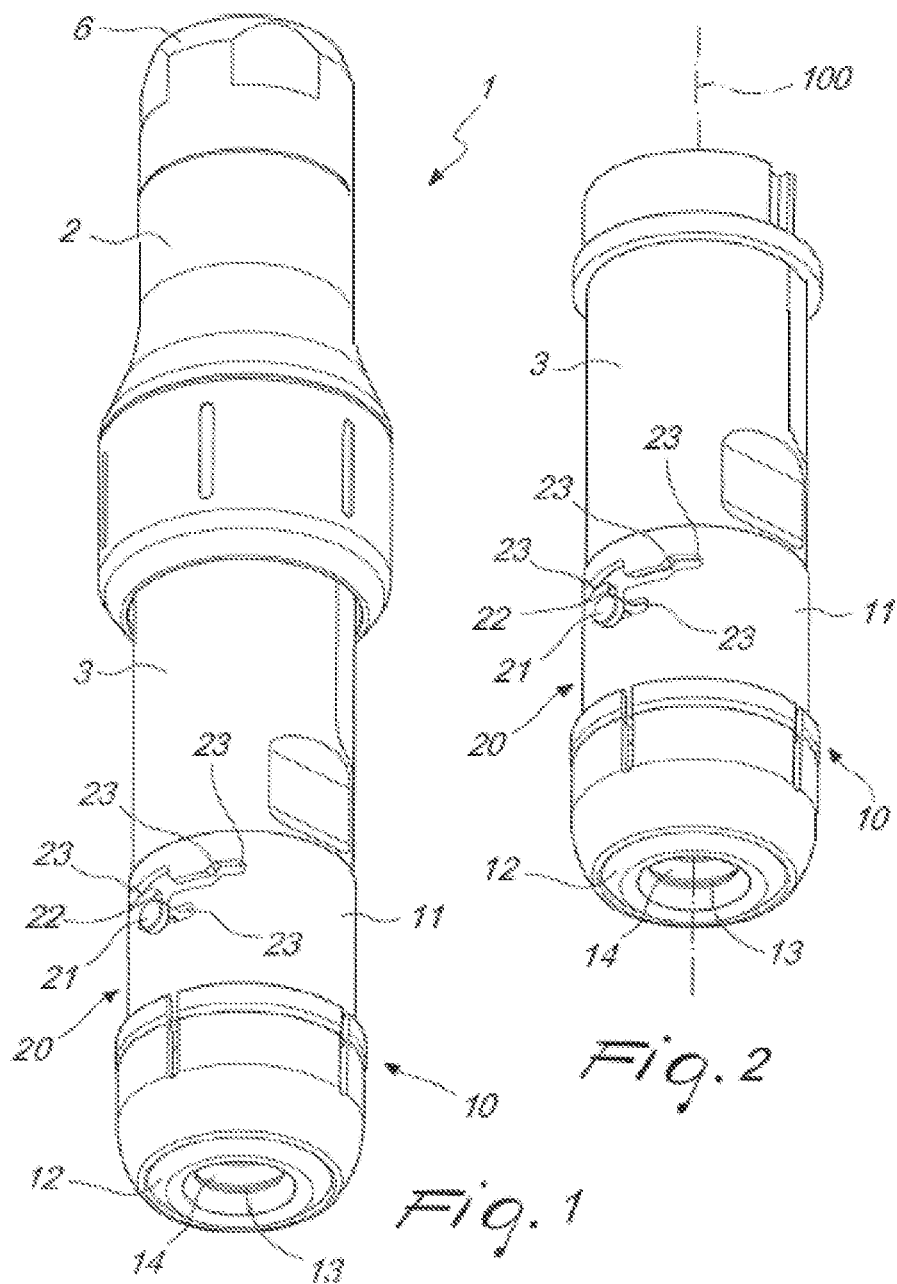

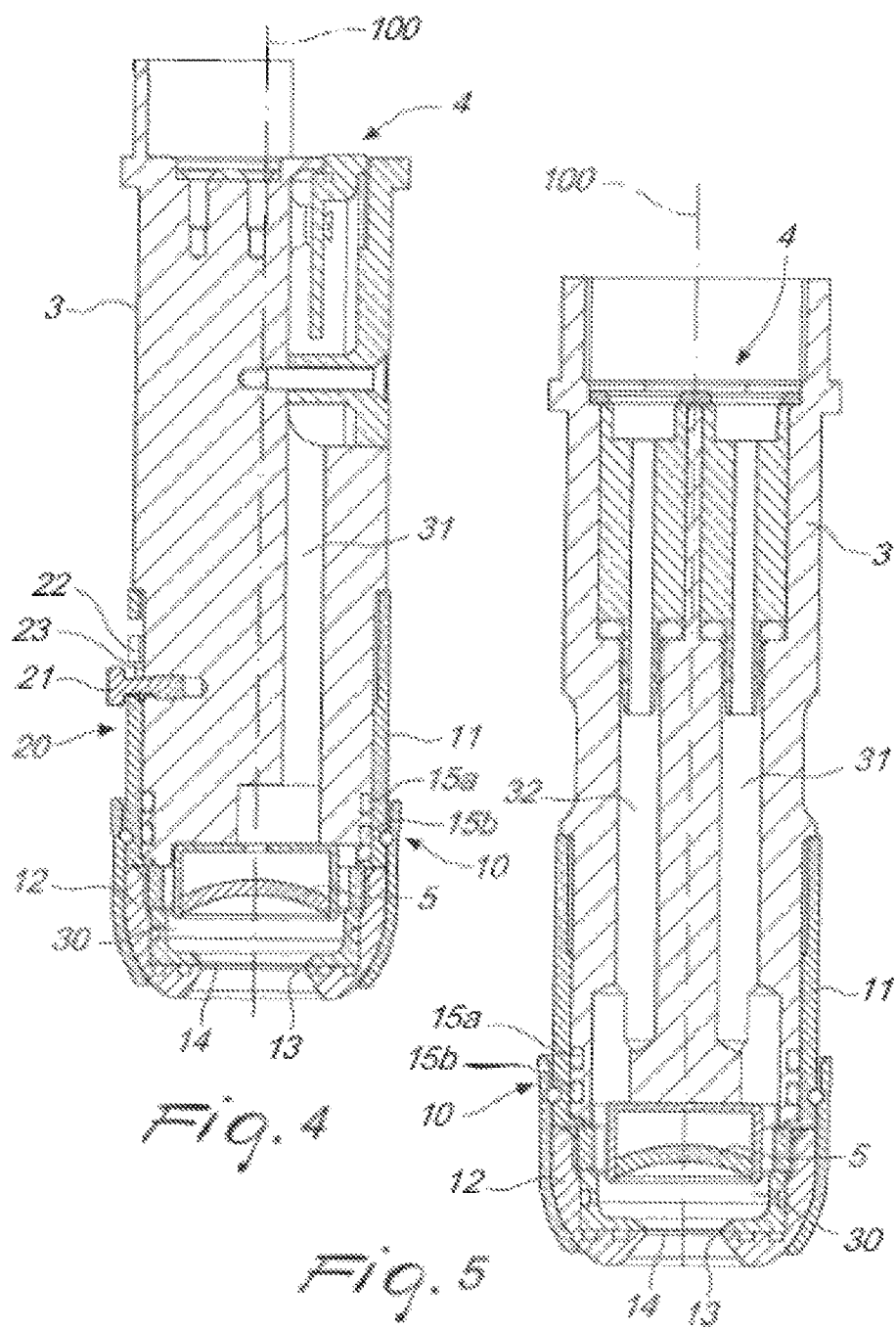

ULTRASOUND PROBE FOR TREATING EXTERNAL BODY TISSUES

CROSS-REFERENCE TO RELATED APPLICATIONS

This application is a § 371 national stage entry of International Application No. PCT/IT2019/000004, filed Jan. 28, 2019, the entire contents of which are incorporated herein by reference.

The present invention relates to an ultrasound probe for treating body tissues.

As is known, currently there are many methods and apparatuses for dealing with and solving problems linked to skin blemishes, such as for example wrinkles, scars and lack of skin tonicity.

Among the various technologies used, techniques for treating skin with high-intensity focused ultrasound (HIFU) are becoming increasingly important.

HIFU technology, developed initially for the treatment of various oncologic pathologies, is currently used in the beauty sector to induce a temperature increase, at different skin depths, such as to create a targeted thermal damage which destroys the target tissue and promotes the forming of new fibers capable of filling the lesion.

The concept on which the use of high-intensity focused ultrasound is based is fundamentally the concept of tissue thermoablation, obtained by converting into heat the energy carried by an elastic wave that is focused on the cells to be treated.

The elastic wave is generated by an ultrasound wave transducer which is usually constituted by a spherical dome made of piezoelectric material; the dome is conceived so as to concentrate the emitted energy in a limited region, commonly termed focal point.

The focal distance, i.e., the distance between the surface of the emitter and the focal point, is a construction parameter that characterizes every ultrasound wave transducer and directly conditions the penetration depth of the focused ultrasound in the tissues.

Accordingly, in order to perform treatments at different depths, currently it is necessary to use ultrasound transducers with different focal distances.

In practice, therefore, it is indispensable to replace the ultrasound wave transducer every time that the treatment is changed, and in some cases even several times during the same session.

This obviously entails drawbacks, both in terms of time and in terms of costs.

It should also be noted that since air is an almost totally reflective medium for ultrasounds, ultrasound transducers are generally contained in hermetically closed chambers filled with water.

However, while on the one hand water ensures the acoustic coupling of the ultrasound wave transducer with the skin of the patient, on the other hand the energy flow entails the heating of the water, causing phenomena such as the forming of air bubbles or the creation of convective motions in the chamber.

These alterations of the state of the liquid interfere with the transmission of the elastic wave.

Also, the heat accumulation of the water contained in the chamber tends to heat the ultrasound wave transducer, with the risk of causing unwanted frequency switches or other operating anomalies.

WO2012/120495 discloses an apparatus having an ultrasound transducer configured to be positioned within a lumen of a subject and to ablate tissue surrounding a wall of the lumen without ablating the wall of the lumen, by focusing ultrasound energy on a focal zone that is outside of the wall of the lumen. A transluminal delivery tool is configured to position the ultrasound transducer in the lumen, and a control unit is configured to drive the ultrasound transducer.

U.S. Pat. No. 5,762,066 discloses a High Intensity focused ultrasound system having an intracavity probe having two active ultrasound radiating surfaces with different focal geometries. Selectively energizing the first surface focuses therapeutic energy a first distance from the housing, energizing the second surface focuses therapeutic energy nearer the housing. The probe includes a thin, flexible, inelastic membrane which is rigidized with pressure to allow blunt manipulation of tissue.

WO2017/200246 discloses an ultrasonic cartridge housing having an ultrasonic transducer unit; the cartridge stores a liquid and has an ultrasonic wave transmission window on the lower surface thereof, is divided into an upper housing member provided with the ultrasonic transducer unit and a lower housing member provided with the ultrasonic wave transmission window, and a distance between the ultrasonic transducer unit and the ultrasonic wave transmission window is adjusted, such that the depth of focus of ultrasonic waves in the skin can be controlled.

EP2422708 discloses a multi-focus probe that includes a motor communicatively coupled with a lead screw and configured to turn the lead screw about a lengthwise axis of the lead screw), wherein the lead screw includes a length having threads. The probe also includes a lead-screw nut positioned about the lead screw such that the lead-screw nut engages the threads and such that the lead-screw nut and the lead screw can move relative to one another via the threads, a transducer configured to move vertically with the lead screw, and an enclosure surrounding the transducer, wherein the enclosure includes a probe face configured to hold fluid and engage a wave emission target such that waves from the transducer can enter the target. The probe also includes a capture feature capable of engaging the lead-screw nut such that the lead-screw nut is vertically fixed relative to the probe face and such that the lead screw moves away from the probe face when rotating within the lead-screw nut in a first direction and moves toward the probe face when rotating within the lead-screw nut in a second direction opposite to the first direction while the lead-screw nut is engaged by the capture feature.

The aim of the present invention is to provide an ultrasound probe for the treatment of body tissues that overcomes the drawbacks of the cited prior art.

Within the scope of this aim, a particular object of the invention is to provide a probe that allows to perform treatments at different skin depths without having to change the ultrasound wave transducer each time.

Another object of the invention is to provide a probe that allows to perform multiple types of treatment.

A further object of the invention is to provide a probe in which attenuation and reflection during the HIFU application are minimal and at the same time unwanted alterations of the transmission medium are avoided.

Another object of the invention is to provide a probe which, by virtue of its particular constructive characteristics, is capable of giving the greatest assurances of reliability and safety in use.

Another object of the invention is to provide a probe that is relatively simple to manufacture and is also competitive from an economic standpoint.

This aim, these objects and others which will become better apparent hereinafter are achieved by an ultrasound probe for treating body tissues, as claimed in the appended claims.

Further characteristics and advantages will become better apparent from the description of a preferred but not exclusive embodiment of a probe according to the invention, illustrated by way of non-limiting example in the accompanying drawings, wherein:

FIG. 1 is a perspective view of a probe according to the invention;

FIG. 2 is a perspective view of a component of the probe according to the invention;

FIG. 4 is an axial sectional view of the component of FIG. 2;

FIG. 5 is another axial sectional view of the component of FIG. 2;

Figure 3:
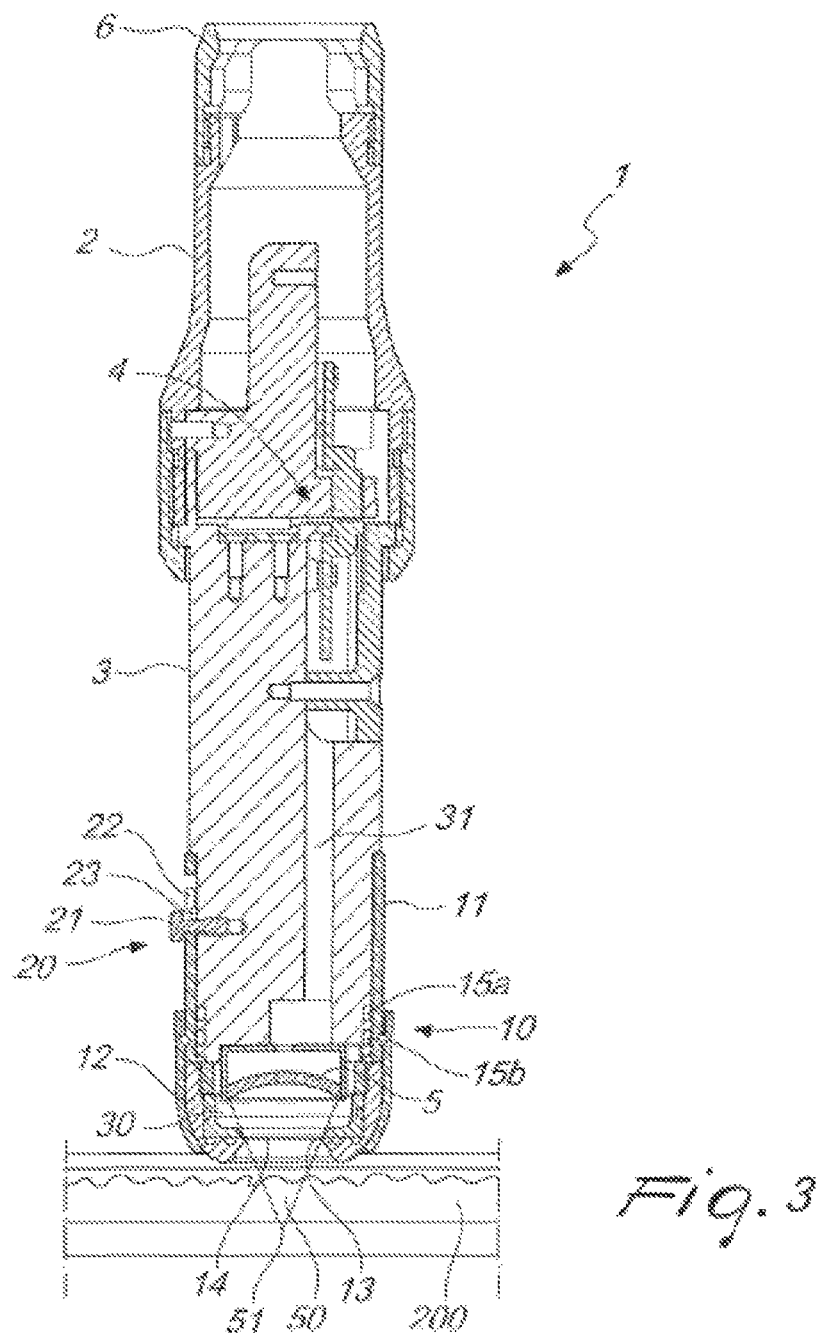
FIG. 3 is an axial sectional view of the probe according to the invention, shown in an example of use.
Figure 6:
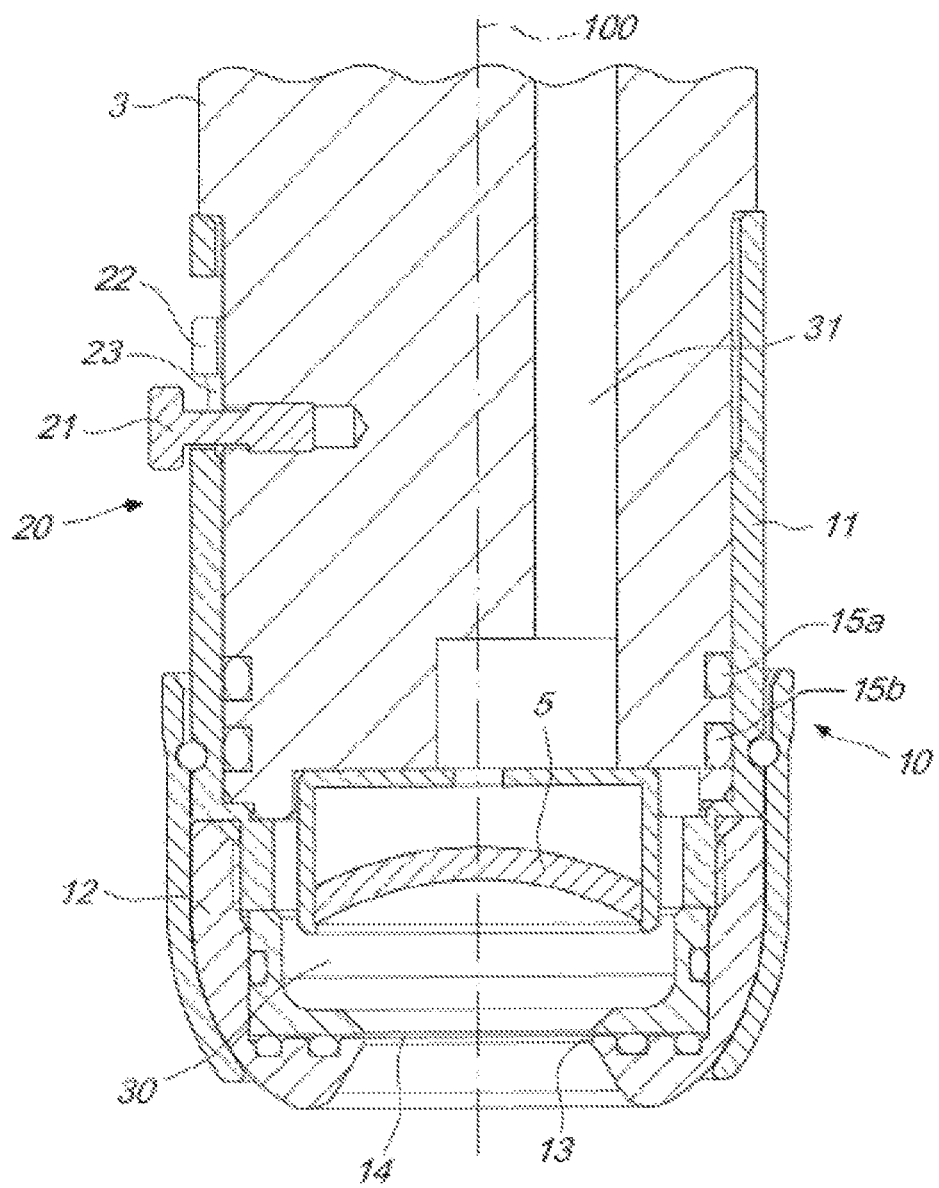
FIG. 6 is an enlarged-scale view of a detail of FIG. 4.

With reference to the cited figures, an ultrasound probe, particularly for treating body tissues, is designated generally by the reference numeral 1.

The probe 1 includes a main body 2 which forms a portion that can be gripped and an end portion 3; the end portion 3 has a substantially cylindrical shape and an axis 100.

Preferably, the end portion 3 is joined to the main body 2 detachably, by virtue of an engagement and disengagement means 4 which allows its interchangeability.

A focused ultrasound emitter is arranged in the end portion 3. The focused ultrasound emitter includes an ultrasound transducer 5, in particular of a type suitable for generating high intensity focused ultrasound (HIFU).

For example, the ultrasound transducer 5 can be constituted by a hemispherical dome that has a monolithic structure and is made of a material having piezoelectric properties.

The ultrasound transducer 5 is powered and controlled by appropriate devices, such as for example a driver and an electronic controller, which are not shown in the figures. These devices are preferably installed in a remote unit, not shown in the figures.

The probe 1 can be connected to the remote unit by a connecting means 6.

According to the present invention, the probe 1 includes an adjustment means 10 for adjusting the penetration depth. The adjustment means 10 adjusts the penetration depth of a beam 50 of focused ultrasound, emitted by the ultrasound transducer 5, in a tissue 200 to be treated, in particular in an epithelial tissue.

In practice, the adjustment means 10 allows to adjust axially the position of the focal point 51 of the focused ultrasound beam 50 with respect to the surface of a tissue 200 on which the probe 1 is rested in order to perform a treatment.

The expressions "axially" or "axial" herein generally refer to a direction that is substantially parallel to the axis of extension 100 of the end portion 3.

The adjustment means 10 includes a terminal member 11 which can move axially with respect to the end portion 3 of the main body 2.

Specifically, the terminal member 11 essentially consists of a cylindrical sleeve which has a substantially cylindrical side wall, which is mounted coaxially on the end portion 3, and an end wall 12, which is substantially dome-shaped.

The relative axial sliding between the terminal member 11 and the end portion 3 can be locked reversibly by virtue of a locking means 20.

Preferably, the locking means 20 are configured in such a manner that the relative locking between the terminal member 11 and the end portion 3 occurs at a position that is chosen from a plurality of predetermined positions.

In the specific case, the locking means 20 include a pin 21 which protrudes radially from the end portion 3 and engages slidingly in a contoured slot 22 provided on the side wall of the terminal member 11.

Advantageously, the contoured slot 22 is extended parallel to the axis 100 and has a plurality of transverse seats 23 for the pin 21.

The transverse seats 23 are mutually spaced axially, so as to define respectively the positions of relative locking between the terminal member 11 and the end portion 3.

In the example of embodiment shown in the figures, the transverse seats 23 are six; however, these seats may vary in number and shape, so long as they in any case ensure a sufficient number of work positions and optimum locking of the pin 21.

Conveniently, the contoured slot 22 is provided with a graduation, not shown in the figures, which distinguishes each transverse seat 23 in such a manner as to indicate to an operator the functional configuration of the probe 1.

The terminal member 11 forms a chamber 30 together with the end portion 3. The chamber 30 has a variable volume and the ultrasound transducer 5 is arranged inside it.

More precisely, the chamber 30 is delimited laterally by the side wall of the terminal member 11, at one axial end by the end wall 12 of the terminal member 11 and at the opposite axial and by the ultrasound transducer 5.

Conveniently, the end wall 12 is provided with a window 13 that has a substantially circular shape and is closed by a membrane 14 made of a material that is substantially flexible and transparent to ultrasound.

In practice, the window 13 has the purpose of allowing the focused ultrasound beam emitted by the ultrasound transducer 5 to penetrate the tissue to be treated.

Advantageously, the chamber 30 is fluid-tight and is filled with a liquid, in the specific case water, which ensures acoustic coupling with the tissue to be treated.

In the specific case, in order to ensure the tightness of the chamber 30, sealing gaskets 15a and 15b, such as for example O-rings, are arranged between the end portion 3 and the terminal member 11.

According to a further aspect of the invention, the water that fills the chamber 30 is replaced continuously in order to eliminate the heat generated by the ultrasound.

Efficient heat removal allows to ensure both durable and correct operation of the ultrasound transducer 5, avoiding for example unwanted frequency switches, and to avoid the forming of bubbles and/or convective motions in the liquid that fills the chamber 30.

Also, by avoiding the overheating of the liquid contained in the chamber 30, the overheating of the end wall 12, which is in contact with the tissue to be treated and might thus cause discomfort to the patient, is also avoided.

The liquid is fed by a pumping device, not visible in the figures, which is connected to the chamber 30 by intake and discharge ducts, designated respectively by 31 and 32, which extend within the main body 2 and in the end portion 3.

The operation of the ultrasound probe according to the present invention is simple and intuitive.

Initially, the operator checks the operating configuration of the probe 1, i.e., detects the axial position of the terminal member 11 with respect to the end portion 3, using also the graduation that distinguishes each transverse seat 23.

Then, if the operator deems it necessary to change the depth of the focal point 51 of the focused ultrasound beam 50 with respect to the surface of the tissue 200 to be treated, the operator sets the probe 1 by acting on the adjustment means 10.

More particularly, the operator must first rotate slightly the terminal member 11 with respect to the end portion 3, so as to disengage the pin 21 from the transverse seat 23 that accommodates it.

Once the pin 21 has been disengaged from the transverse seat 23, it is possible to make it slide within the contoured slot 22, causing the axial sliding of the terminal member 11 with respect to the end portion 3.

After identifying the correct relative position between the end portion 3 and the terminal member 11, the terminal member 11 is again rotated with respect to the end portion 3, so as to engage again the pin 21 in another transverse seat 23.

In order to increase the depth of the focal point 51 of the focused ultrasound beam 50 with respects to the surface of the tissue 200 to be treated it is necessary to retract the terminal member 11 with respect to the end portion 3, whereas in order to decrease the depth of the focal point 51 it is necessary to extract the terminal member 11 with respect to the end portion 3.

When the probe 1 is configured correctly, the operator places the probe on the tissue 200 to be treated, preferably keeping the axis 100 of the terminal portion 3 substantially perpendicular to the surface of the tissue 200 to be treated, and starts dispensing the focused ultrasound beam 50.

The pumping device also begins operating simultaneously with the ultrasound transducer 50 and, by means of the intake duct 31 and discharge duct 32, changes continuously the liquid that fills the chamber 30, with all the advantages that have already been described.

In practice it has been found that the invention achieves the intended aim and objects, an ultrasound probe for treating body tissues having been provided which allows to perform treatments at different skin depths without having to change the ultrasound wave transducer each time.

The probe according to the invention in fact allows to vary simply and repeatably the position of the focal point in the tissue, so as to be able to choose among multiple types of treatment without changing device.

Also, the probe according to the invention allows to minimize attenuation and reflection during the application of the HIFU and simultaneously to avoid the forming of bubbles or convective motions in the transmission medium.

The materials used, so long as they are compatible with the specific use, as well as the contingent shapes and dimensions, may of course vary according to the requirements and the state of the art.

The invention claimed is:

1. An ultrasound probe for treating external body tissues of a body on their surface and at various depths, the ultrasound probe configured to treat the external body tissues from a location that is outside of the body, the ultrasound probe, comprising at least one focused ultrasound emitter, said emitter being arranged within a main body which forms a portion that can be gripped, said probe further comprising a means for connection to a remote unit for the power supply and control of said probe, said probe further comprising a penetration depth adjustment means for adjusting the penetration depth of a beam of focused ultrasound emitted by said emitter; said penetration depth adjustment means comprising a terminal member which can move axially with respect to an end portion of said main body; said probe comprising a locking means adapted to lock the relative axial movement between said terminal member and said main body; said terminal member comprising a cylindrical side wall and an end wall, said side wall being associated slidingly and coaxially with said end portion of said main body, said end portion having a cylindrical shape; said focused ultrasound emitter comprising an ultrasound transducer arranged inside a variable-volume chamber formed at said end portion of said main body; said chamber being at least partly delimited by said side wall of said terminal member and by said end wall of said terminal member; said end wall being provided with a window that is closed by a membrane which is flexible and transparent to ultrasound; said probe being characterized in that said chamber is fluid-tight and configured to contain a liquid that can be replaced continuously; said liquid being fed by a pumping device which is connected to said chamber by means of intake and discharge ducts.

2. The probe according to claim 1, wherein said locking means is configured to lock the relative axial sliding between said terminal member and said main body at a position chosen from a plurality of predetermined positions.

3. The probe according to claim 2, wherein said locking means comprises at least one pin which protrudes from said end portion of said main body and is engaged slidingly in a contoured slot provided on said side wall of said terminal member, said contoured slot extending substantially axially and having a plurality of transverse seats for said at least one pin; said transverse seats being mutually spaced axially in order to define respectively said plurality of predetermined positions.

4. The probe according to claim 1, wherein said ultrasound transducer is suitable for generating high intensity focused ultrasound.

5. The probe according to claim 1, wherein said end portion is joined to said main body detachably, by virtue of an engagement/disengagement means which allows its interchangeability.

6. The probe according to claim 1, wherein the body tissues comprise skin.

7. The probe according to claim 6, wherein said end wall is configured to contact the skin.

* * * * *